US009365349B1

(12) United States Patent
Strybos

(10) Patent No.: US 9,365,349 B1
(45) Date of Patent: Jun. 14, 2016

(54) USE OF MULTIPLE STORAGE CAVERNS FOR PRODUCT IMPURITY CONTROL

(71) Applicant: Air Liquide Large Industries U.S. LP, Houston, TX (US)

(72) Inventor: Ronald Strybos, Kountze, TX (US)

(73) Assignee: Air Liquide Large Industries U.S. LP, Houston, TX (US)

(*) Notice: Subject to any disclaimer, the term of this patent is extended or adjusted under 35 U.S.C. 154(b) by 0 days.

(21) Appl. No.: 14/943,851

(22) Filed: Nov. 17, 2015

(51) Int. Cl.
*B65G 5/00* (2006.01)
*G01N 33/00* (2006.01)

(52) U.S. Cl.
CPC .............. *B65G 5/00* (2013.01); *G01N 33/0036* (2013.01); *F17C 2270/0152* (2013.01); *G01N 33/004* (2013.01); *G01N 33/0044* (2013.01); *G01N 33/0047* (2013.01)

(58) Field of Classification Search
CPC .......... G01N 33/0036; G01N 33/0044; G01N 33/004; G01N 33/0047; B65G 5/00; F17C 2270/0152; F17C 2260/015; F17C 2260/017
See application file for complete search history.

(56) References Cited

U.S. PATENT DOCUMENTS

| 1,923,896 A | 8/1933 | Trump |
| 2,009,534 A | 7/1935 | Trump |
| 2,073,053 A | 3/1937 | Ducommun et al. |
| 2,229,140 A | 1/1941 | Smith et al. |
| 2,284,869 A | 6/1942 | Hinderliter |
| 2,346,392 A | 4/1944 | Protin et al. |
| 2,402,862 A | 6/1946 | Wright |
| 2,787,455 A | 4/1957 | Knappen |
| 2,878,165 A | 3/1959 | Cottle |
| 3,056,265 A | 10/1962 | Swinney |
| 3,148,000 A | 9/1964 | Dahms et al. |

(Continued)

FOREIGN PATENT DOCUMENTS

| DE | 101 17 617 | 10/2002 |
| EP | 0 086 506 | 8/1983 |

(Continued)

OTHER PUBLICATIONS

Thompson, James M. "US Underground Storage of Natural Gas in 1997: Existing and Proposed." Natural Gas Monthly, United States Energy Information Administration (1997).*

(Continued)

*Primary Examiner* — Lisa Caputo
*Assistant Examiner* — Punam Roy
(74) *Attorney, Agent, or Firm* — Elwood L. Haynes

(57) ABSTRACT

An inventory management method is also provided. This method includes removing and replacing the gas product from a first salt cavern as supply and demand dictate, analyzing the impurities in the gas product that is removed, predicting the duration until a maximum acceptable impurity limit is present, removing all the working gas from the first salt cavern when the maximum acceptable impurity limit is reached, then replacing the working gas in the first salt cavern, while concurrently, removing and replacing the gas product from a second salt cavern as supply and demand dictate, analyzing the impurities in the gas product that is removed, predicting the duration until a maximum acceptable impurity limit is present, removing all the working gas from the second salt cavern when the maximum acceptable impurity limit is reached, then replacing the working gas in the second salt cavern, while concurrently repeating steps a)-g).

9 Claims, 3 Drawing Sheets

(56) References Cited

U.S. PATENT DOCUMENTS

| | | | |
|---|---|---|---|
| 3,289,609 A | 12/1966 | Palo | |
| 3,384,133 A * | 5/1968 | Gordon | F17C 13/04 137/510 |
| 3,438,203 A | 4/1969 | Lamb et al. | |
| 3,807,181 A | 4/1974 | Kuhne | |
| 3,848,427 A | 11/1974 | Loofbourow | |
| 4,342,911 A | 8/1982 | French | |
| 4,365,978 A | 12/1982 | Scott | |
| 4,377,397 A | 3/1983 | Clements | |
| 4,422,859 A | 12/1983 | McGee | |
| 4,538,414 A | 9/1985 | Saleh | |
| 4,592,677 A | 6/1986 | Washer | |
| 4,616,669 A | 10/1986 | Washer et al. | |
| 4,632,601 A | 12/1986 | Kuwada | |
| 4,720,995 A | 1/1988 | Thiel | |
| 4,789,101 A | 12/1988 | Kempf | |
| 4,919,822 A | 4/1990 | Boulanger | |
| 5,207,530 A | 5/1993 | Brooks et al. | |
| 5,246,273 A | 9/1993 | Rosar | |
| 5,333,465 A | 8/1994 | McBride | |
| 5,336,083 A | 8/1994 | Rajewski | |
| 5,431,482 A | 7/1995 | Russo | |
| 5,486,811 A | 1/1996 | Wehrle et al. | |
| 5,495,893 A | 3/1996 | Roberts et al. | |
| 5,511,905 A | 4/1996 | Bishop et al. | |
| 5,957,539 A | 9/1999 | Durup et al. | |
| 6,412,508 B1 | 7/2002 | Swann | |
| 6,527,002 B1 | 3/2003 | Szakaly | |
| 6,579,454 B2 | 6/2003 | Kaske | |
| 7,078,011 B2 | 7/2006 | Morrow et al. | |
| 7,097,386 B2 | 8/2006 | Maduell et al. | |
| 7,152,675 B2 | 12/2006 | Heard | |
| 7,905,251 B2 | 3/2011 | Flanders | |
| 8,002,498 B2 | 8/2011 | Leone et al. | |
| 8,757,926 B2 | 6/2014 | Drnevich | |
| 8,814,133 B2 | 8/2014 | Li et al. | |
| 2002/0174895 A1 | 11/2002 | Hill et al. | |
| 2003/0025381 A1 | 2/2003 | Pickren | |
| 2004/0238081 A1 | 12/2004 | Yoshinaga et al. | |
| 2005/0220704 A1 | 10/2005 | Morrow et al. | |
| 2006/0150640 A1 | 7/2006 | Bishop | |
| 2008/0127654 A1 | 6/2008 | Darling et al. | |
| 2008/0257542 A1 | 10/2008 | Brisco et al. | |
| 2009/0010714 A1 | 1/2009 | Bishop | |
| 2010/0276156 A1 | 11/2010 | Jennings | |
| 2011/0100213 A1 | 5/2011 | Finkenrath et al. | |
| 2011/0127825 A1 | 6/2011 | Hughes et al. | |
| 2011/0305515 A1 | 12/2011 | Drnevich | |
| 2012/0174569 A1 | 7/2012 | Ingersoll et al. | |
| 2013/0213479 A1 | 8/2013 | Oates et al. | |
| 2013/0315669 A1 | 11/2013 | Oates | |
| 2014/0241802 A1 | 8/2014 | Drnevich | |
| 2015/0137578 A1 | 5/2015 | Colomé | |

FOREIGN PATENT DOCUMENTS

| | | |
|---|---|---|
| GB | 2 460 550 | 12/2009 |
| WO | WO 2013 173709 | 11/2013 |

OTHER PUBLICATIONS

Barron, T.F., "Regulatory, technical pressures prompt more U.S. salt-cavern gas storage," Oil and Gas Journal, Pennwell, Houston, TX, US, vol. 92, No. 37, Sep. 12, 1994, 55-67.

Berest, P., "International Gas Union Research Conference 2011: Thermomechanical aspects of high frequency cycling in salt storage caverns," 2011, 22 pgs.

Devries, K.L. et al., "Cavern roof stability for natural gas storage in bedded salt," Jun. 2005, 191 pgs.

Electric Power Research Institute, "Carbon Steel Handbook," Mar. 2007, 172 pgs.

Flowserve, "Forged Steel ASMT A350 Grade LF2 Valves," webpage, 2009, 2 pgs.

Fomas Group, "Oil and Gas," brochure, 2015, 24 pgs.

Pottier, J.D. et al., "Mass storage of hydrogen," Proceedings of the NATO Advanced Study Institute series, Series E, Applied Sciences; Hydrogen Energy System: Production and Utilization of Hydrogen and Future Aspects, vol. 295, Jan. 1, 1995, 167-179.

Welker Engineering, "Particular Material Appraisal Grade LF2 Class 1 According to ASME SA-350," Jun. 2, 2004, 3 pgs.

International Search Report and Written Opinion for related PCT/US2015/029400, Jul. 21, 2015.

International Search Report and Written Opinion for related PCT/US2015/029662, Jul. 29, 2015.

International Search Report and Written Opinion for related PCT/US2015/029646, Nov. 13, 2015.

* cited by examiner

USE OF MULTIPLE STORAGE CAVERNS FOR PRODUCT IMPURITY CONTROL

BACKGROUND

The storage of gases and liquids in solution mined salt caverns, whether leached in domal or stratified salt formations or can result in contamination of the stored product by, for example, egress of impurities from the salt formation and overburden outside the salt formation. The stored products typically include hydrogen, nitrogen, carbon dioxide, air, methane, ethane, ethylene, propylene, propane, ethane/propane mix (LPG), butane, or pentane.

Typical impurities include, but are not limited to, hydrogen sulfide ($H_2S$), methane ($CH_4$), carbon dioxide ($CO_2$), nitrogen ($N_2$), ethane ($C_2H_6$), benzene ($C_6H_6$) and other naturally occurring hydrocarbons ($C_xH_x$). These impurities were found to enter the salt cavern from two sources, either gas bubbles trapped in the salt formation or methane gas entering the cavern through fractures and weak seams In a single cavern storage configuration, it was found that impurities accumulate in the stored product and increase over time, causing the product to not meet commercial specification.

SUMMARY

One embodiment of an inventory management method is provided. This method includes introducing a gas product into a first salt cavern and a second salt cavern, removing and replacing the gas product from the first salt cavern as supply and demand dictate, analyzing the impurities in the gas product that is removed, predicting the duration until a maximum acceptable impurity limit is present, removing all the working gas from the first salt cavern when the maximum acceptable impurity limit is reached, then replacing the working gas in the first salt cavern, while concurrently, removing and replacing the gas product from the second salt cavern as supply and demand dictate, analyzing the impurities in the gas product that is removed, predicting the duration until a maximum acceptable impurity limit is present, removing all the working gas from the second salt cavern when the maximum acceptable impurity limit is reached, then replacing the working gas in the second salt cavern, while concurrently repeating steps b)-h).

Another embodiment of an inventory management method is also provided. This method includes removing and replacing the gas product from a first salt cavern as supply and demand dictate, analyzing the impurities in the gas product that is removed, predicting the duration until a maximum acceptable impurity limit is present, removing all the working gas from the first salt cavern when the maximum acceptable impurity limit is reached, then replacing the working gas in the first salt cavern, while concurrently, removing and replacing the gas product from ae second salt cavern as supply and demand dictate, analyzing the impurities in the gas product that is removed, predicting the duration until a maximum acceptable impurity limit is present, removing all the working gas from the second salt cavern when the maximum acceptable impurity limit is reached, then replacing the working gas in the second salt cavern, while concurrently repeating steps a)-g).

Another embodiment of an inventory management method is provided. This method includes introducing a gas product into a first salt cavern and a second salt cavern, analyzing the impurities in the gas product, predicting the duration until a maximum acceptable impurity limit is present, removing and replacing the gas product from the first salt cavern as supply and demand dictate, removing all the working gas from the first salt cavern when the predicted maximum acceptable impurity limit duration is reached, then replacing the working gas in the first salt cavern, while concurrently, removing and replacing the gas product from the second salt cavern as supply and demand dictate, removing all the working gas from the second salt cavern when the predicted maximum acceptable impurity limit duration is reached, then replacing the working gas from the second salt cavern, while concurrently repeating steps b)-f).

Another embodiment of an inventory management method is provided. This method includes analyzing the impurities in the gas product, predicting the duration until a maximum acceptable impurity limit is present, removing and replacing the gas product from the first salt cavern as supply and demand dictate, removing all the working gas from the first salt cavern when the predicted maximum acceptable impurity limit duration is reached, then replacing the working gas in the first salt cavern, while concurrently, removing and replacing the gas product from the second salt cavern as supply and demand dictate, removing all the working gas from the second salt cavern when the predicted maximum acceptable impurity limit duration is reached, then replacing the working gas from the second salt cavern, while concurrently repeating steps b)-e).

Another embodiment of an inventory management method is provided. This method includes introducing a gas product into Q salt caverns, where Q is a number greater than 1, setting cavern counter N to 0, if N=Q, setting salt cavern counter to N=0, if N<Q, setting salt cavern counter to N=N+1, removing and replacing the gas product from salt cavern N as supply and demand dictate, analyzing the impurities in the gas product that is removed from salt cavern N, predicting the duration until a maximum acceptable impurity limit is present in the product gas removed from cavern N, removing all the working gas from salt cavern N when the maximum acceptable impurity limit is reached, then replacing the working gas in salt cavern N, while concurrently, repeating steps b)-f).

Another embodiment of an inventory management method is provided. This method includes if N=Q, setting salt cavern counter to N=0, if N<Q, setting salt cavern counter to N=N+1, removing and replacing the gas product from salt cavern N as supply and demand dictate, analyzing the impurities in the gas product that is removed from salt cavern N, predicting the duration until a maximum acceptable impurity limit is present in the product gas removed from cavern N, removing all the working gas from salt cavern N when the maximum acceptable impurity limit is reached, then replacing the working gas in salt cavern N, while concurrently, repeating steps a)-e).

The gas product may be selected from the group consisting of hydrogen, nitrogen, carbon dioxide, air, methane, ethane, ethylene, propylene, propane, ethane/propane mix, butane, and pentane. The impurities may be selected from the group consisting of hydrogen sulfide, methane, carbon dioxide, nitrogen, ethane, and benzene.

DESCRIPTION OF PREFERRED EMBODIMENTS

Figure 1:
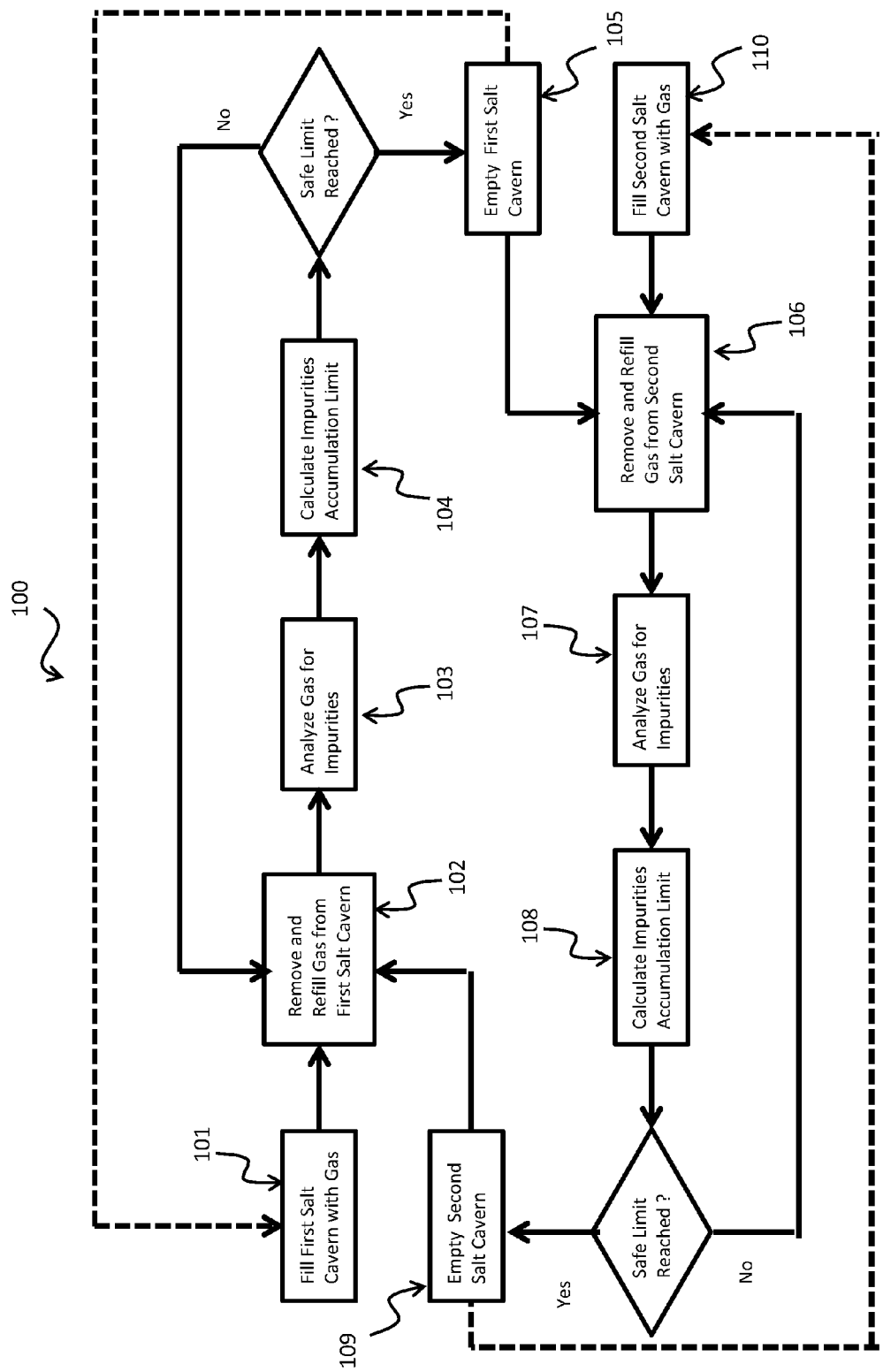
FIG. 1 illustrates one embodiment of the present invention.

Illustrative embodiments of the invention are described below. While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

In a single cavern storage configuration, it was found that impurities accumulate in the stored product and increase over time, causing the product to not meet commercial specification. This invention claims that by utilizing an inventory management system and multiple caverns the impurity concentrations are minimized. Multiple caverns can be 2 or more caverns that the same products are stored in. The caverns are connected on the surface by pipeline and pump or compressor stations.

Definitions of terms used herein:

Primary cavern—the main cavern used to store products and provide products to customers.

Reserve cavern—the cavern used as the back up to store products and provide products to customers.

Base gas—the volume of gas that is the permanent inventory of the cavern, and is used to maintain adequate minimum pressure within the cavern.

Working gas—the volume of gas in the cavern in addition to the base gas, and is available to supply customer demands.

Turning now to FIG. 1, one embodiment of an inventory management method 100 is provided. As shown in FIG. 1, the method 100 includes introducing a gas product into a first salt cavern 101 and a second salt cavern 110. The gas product can be hydrogen, nitrogen, carbon dioxide, air, methane, ethane, ethylene, propylene, propane, ethane/propane mix, butane, or pentane. The gas product is introduced to the first salt cavern and stored under pressure.

Under normal operation, the gas product is removed from the first salt cavern during times of high demand and/or low availability, and the gas product is replaced in the first salt cavern during times of low demand and/or high availability 102. Over time, various impurities will accumulate in the gas stored in the first cavern. These impurities may include hydrogen sulfide, methane, carbon dioxide, nitrogen, ethane, and/or benzene. As the gas is removed from the first cavern, the impurities are analyzed 103. A prediction is made based on this analysis, as to the length of time that the first cavern may be operated before a maximum acceptable impurity limit is present in the first cavern 104. This maximum acceptable impurity limit is established based on customer requirements, but will typically be a value below the minimum threshold for these impurities required in the associated pipeline specification.

Once the predicted maximum acceptable impurity limit is reached, all of the working gas is allowed to be removed from the first salt cavern 105. Concurrently, under normal operation, the gas product is now removed from the second salt cavern during times of high demand and/or low availability, and the gas product is replaced in the second salt cavern during times of low demand and/or high availability 106. Once the working gas has been removed, and only the base gas remains, the first cavern is refilled with fresh gas product from the associated pipeline 101.

Now, as the gas is removed from the second cavern, the impurities are analyzed 107. A prediction is made based on this analysis, as to the length of time that the second cavern may be operated before a maximum acceptable impurity limit is present in the second cavern 108. This maximum acceptable impurity limit is established based on customer requirements, but will typically be a value below the minimum threshold for these impurities required in the associated pipeline specification.

Once the predicted maximum acceptable impurity limit is reached, all of the working gas is now allowed to be removed from the second salt cavern 109. Concurrently, under normal operation, the gas product is now removed again from the first salt cavern during times of high demand and/or low availability, and the gas product is replaced in the first salt cavern during times of low demand and/or high availability 102. Once the working gas has been removed, and only the base gas remains, the second cavern is refilled with fresh gas product from the associated pipeline 110. As the gas is removed from the first cavern, the impurities are analyzed 103. And the alternating cycle continues, with each salt cavern being emptied and refilled once the maximum acceptable impurity limit is reached, while the other salt cavern takes over with satisfying customer demands.

Figure 2:
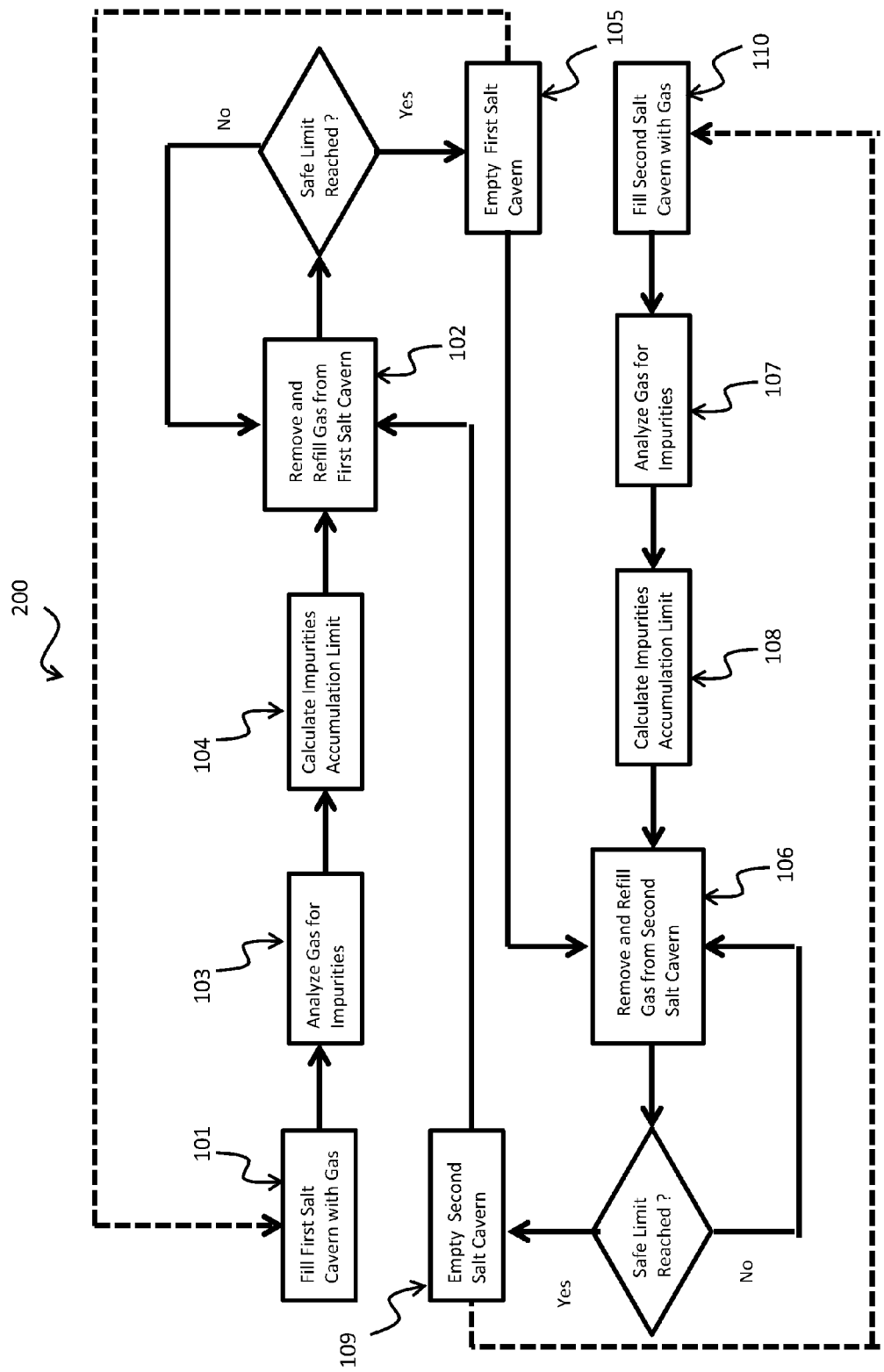
FIG. 2 illustrates another embodiment of the present invention.

Turning now to FIG. 2, another embodiment of an inventory management method 200 is provided. In the interest of clarity, as the various method steps in FIG. 2 are identical to those of FIG. 1, the same element numbers are used.

As shown in FIG. 2, the method 200 includes introducing a gas product into a first salt cavern 101 and a second salt cavern 110. The gas product can be hydrogen, nitrogen, carbon dioxide, air, methane, ethane, ethylene, propylene, propane, ethane/propane mix, butane, or pentane. The gas product is introduced to the first salt cavern and stored under pressure.

Over time, various impurities will accumulate in the gas stored in the first cavern. These impurities may include hydrogen sulfide, methane, carbon dioxide, nitrogen, ethane, and/or benzene. As the gas is removed from the first cavern, the impurities are analyzed 103. A prediction is made based on this analysis, as to the length of time that the first cavern may be operated before a maximum acceptable impurity limit is present in the first cavern 104. This maximum acceptable impurity limit is established based on customer requirements, but will typically be a value below the minimum threshold for these impurities required in the associated pipeline specification.

The difference between inventory management method 100 and inventory management method 200, is that in method 100 the analysis and calculation/prediction of impurities is done as a feedback loop. With each new gas analysis, additional prediction accuracy may be possible. The frequency of the analysis, and hence the frequency with which the impurity prediction is made is a design choice made by the skilled artisan. In method 200, the analysis and calculation/prediction of impurities is done in a feed forward fashion. The analysis is made of the gas, and based, for example, on historical data, the estimated time that the cavern must be discontinued and emptied is predicted.

Under normal operation, the gas product is removed from the first salt cavern during times of high demand and/or low availability, and the gas product is replaced in the first salt cavern during times of low demand and/or high availability 102.

Once the predicted maximum acceptable impurity limit is reached, all of the working gas is allowed to be removed from the first salt cavern 105. Concurrently, the gas is now being removed from the second cavern. As the gas is removed from the second cavern, the impurities are analyzed 107. A prediction is made based on this analysis, as to the length of time that the second cavern may be operated before a maximum acceptable impurity limit is present in the second cavern 108. This maximum acceptable impurity limit is established based on customer requirements, but will typically be a value below the minimum threshold for these impurities required in the associated pipeline specification.

Now, under normal operation, the gas product is removed from the second salt cavern during times of high demand and/or low availability, and the gas product is replaced in the second salt cavern during times of low demand and/or high availability 106. Once the working gas has been removed, and only the base gas remains, the first cavern is refilled with fresh gas product from the associated pipeline 101.

Once the predicted maximum acceptable impurity limit is reached, all of the working gas is now allowed to be removed from the second salt cavern 109. Concurrently, under normal operation, the gas product is now removed again from the first salt cavern, analyzed, impurity threshold predicted, and during times of high demand and/or low availability, and the gas product is replaced in the first salt cavern during times of low demand and/or high availability 102. Once the working gas has been removed, and only the base gas remains, the second cavern is refilled with fresh gas product from the associated pipeline 110. And the alternating cycle continues, with each salt cavern being emptied and refilled once the maximum acceptable impurity limit is reached, while the other salt cavern takes over with satisfying customer demands.

Figure 3:
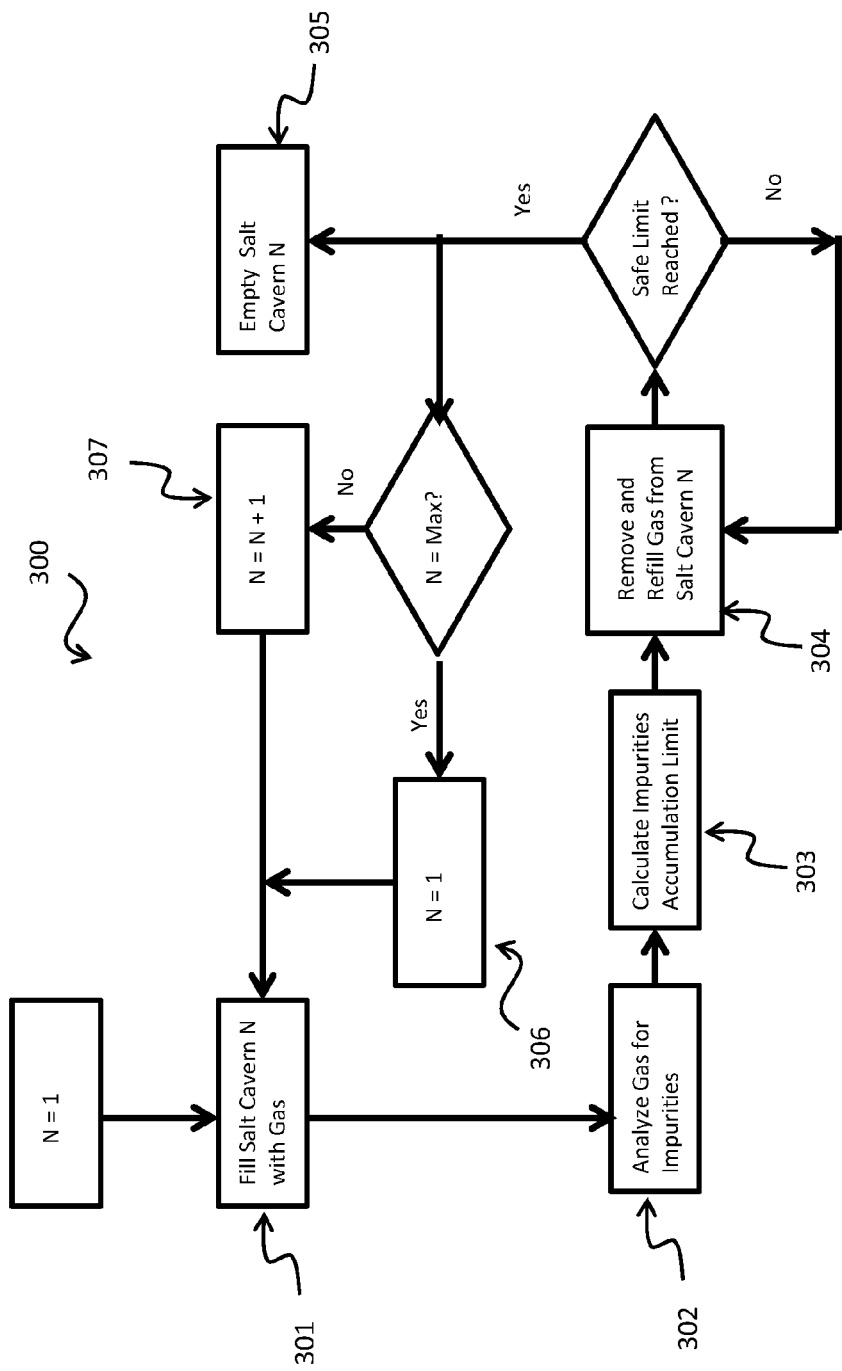
FIG. 3 illustrates another embodiment of the present invention.

Turning now to FIG. 3, another embodiment of an inventory management method 300 is provided. Whereas the method descriptions provided for inventory management methods 100 and 200 were based on the presence of two working salt caverns, inventory management method 300 is more general, and is based on the presence of X caverns, where X is a number greater than 1, which are intended to be used on concert.

The description that follows uses the feed forward model seen above in inventory management present method 200, but one skilled in the art would recognize that this method may also be applied with the feedback model seen above in inventory management method 100.

As shown in FIG. 3, the method 300 includes introducing a gas product into salt cavern N 301. In order to illustrate this system, the initial value for N is established to be 1, and the number of caverns in coordinated operation is 3. For the sake of clarity, as following method is navigated, the current value N will be illustrated in parentheses.

The gas product can be hydrogen, nitrogen, carbon dioxide, air, methane, ethane, ethylene, propylene, propane, ethane/propane mix, butane, or pentane. The gas product is introduced to the first salt cavern and stored under pressure.

Over time, various impurities will accumulate in the gas stored in cavern N (1). These impurities may include hydrogen sulfide, methane, carbon dioxide, nitrogen, ethane, and/or benzene. As the gas is removed from the salt cavern N (1), the impurities are analyzed 302. A prediction is made based on this analysis, as to the length of time that cavern N (1) may be operated before a maximum acceptable impurity limit is present in the cavern N (1) 303. This maximum acceptable impurity limit is established based on customer requirements, but will typically be a value below the minimum threshold for these impurities required in the associated pipeline specification.

Under normal operation, the gas product is removed from salt cavern N (1) during times of high demand and/or low availability, and the gas product is replaced in salt cavern N (1) during times of low demand and/or high availability 304.

Once the predicted maximum acceptable impurity limit is reached, all of the working gas is allowed to be removed from the salt cavern N (1) 305. Now, cavern counter N (1) is either increased by 1 (N=2) (307) or reset to 1 (not applicable for this cycle) (306) depending on which cavern was most recently used and is now being emptied.

Concurrently, the gas is now being removed from the next salt cavern N (2). As the gas is removed from the salt cavern N (2) the impurities are analyzed 302. A prediction is made based on this analysis, as to the length of time that salt cavern N (2) may be operated before a maximum acceptable impurity limit is present in salt cavern N (2) 303. This maximum acceptable impurity limit is established based on customer requirements, but will typically be a value below the minimum threshold for these impurities required in the associated pipeline specification.

Now, under normal operation, the gas product is removed from salt cavern N (2) during times of high demand and/or low availability, and the gas product is replaced in the salt cavern N (2) during times of low demand and/or high availability 304. Once the working gas has been removed from cavern N (1), and only the base gas remains, cavern N (1) is refilled with fresh gas product from the associated pipeline 101.

Once the predicted maximum acceptable impurity limit is reached, all of the working gas is allowed to be removed from the salt cavern N (2) 305. Now, cavern counter N (2) is either increased by 1 (N=3) (307) or reset to 1 (not applicable for this cycle) (306) depending on which cavern was most recently used and is now being emptied.

Concurrently, the gas is now being removed from the next salt cavern N (3). As the gas is removed from the salt cavern N (3) the impurities are analyzed 302. A prediction is made based on this analysis, as to the length of time that salt cavern N (3) may be operated before a maximum acceptable impurity limit is present in salt cavern N (3) 303. This maximum acceptable impurity limit is established based on customer requirements, but will typically be a value below the minimum threshold for these impurities required in the associated pipeline specification.

Now, under normal operation, the gas product is removed from salt cavern N (3) during times of high demand and/or low availability, and the gas product is replaced in the salt cavern N (3) during times of low demand and/or high availability 304. Once the working gas has been removed from cavern N (2), and only the base gas remains, cavern N (2) is refilled with fresh gas product from the associated pipeline 101.

Once the predicted maximum acceptable impurity limit is reached, all of the working gas is allowed to be removed from the salt cavern N (3) 305. Now, cavern counter N (3) is either increased by 1 (not applicable for this cycle) (307) or reset to 1 (applicable for this cycle) (306) depending on which cavern was most recently used and is now being emptied.

Once the working gas has been removed, and only the base gas remains, the next salt cavern in the sequence is refilled with fresh gas product from the associated pipeline 301. And the alternating cycle continues, with each salt cavern being emptied and refilled once the maximum acceptable impurity limit is reached, while the other salt cavern takes over with satisfying customer demands.

The inventory management method essentially includes the following steps:
1. Filling a salt cavern with product.
2. Analyzing the product for impurities.
3. Calculating how long the impurities will accumulate to make the product out of specification.
4. Fill the reserve cavern(s).
5. Empty the primary cavern before the impurity level causes the cavern to go out of specification for impurities.
6. Repeat this process for each cavern to keep inventory within the quality specification.

What is claimed is:

1. An inventory management method, comprising;
   a) introducing a gas product into Q salt caverns, where Q is a number greater than 1, setting cavern counter N to 0,
   b) if N=Q, setting salt cavern counter to N=0,
   c) if N<Q, setting salt cavern counter to N=N+1,
   d) removing and replacing the gas product from salt cavern N as supply and demand dictate,
   e) analyzing the impurities in the gas product that is removed from salt cavern N,
   f) predicting the duration until a maximum acceptable impurity limit is present in the product gas removed from cavern N,
   g) removing all the working gas from salt cavern N when the maximum acceptable impurity limit is reached, then replacing the working gas in salt cavern N, while concurrently, repeating steps b)-f).

2. The inventory management method of claim 1, wherein the gas product is selected from the group consisting of hydrogen, nitrogen, carbon dioxide, air, methane, ethane, ethylene, propylene, propane, ethane/propane mix, butane, and pentane.

3. The inventory management method of claim 1, wherein the gas product is hydrogen.

4. The inventory management method of claim 1, wherein the impurities are selected from the group consisting of hydrogen sulfide, methane, carbon dioxide, nitrogen, ethane, and benzene.

5. An inventory management method, comprising;
   a) if N=Q, setting salt cavern counter to N=0,
   b) if N<Q, setting salt cavern counter to N=N+1,
   c) removing and replacing the gas product from salt cavern N as supply and demand dictate,
   d) analyzing the impurities in the gas product that is removed from salt cavern N,
   e) predicting the duration until a maximum acceptable impurity limit is present in the product gas removed from cavern N,
   f) removing all the working gas from salt cavern N when the maximum acceptable impurity limit is reached, then replacing the working gas in salt cavern N, while concurrently, repeating steps a)-e).

6. The inventory management method of claim 5, wherein the gas product is selected from the group consisting of hydrogen, nitrogen, carbon dioxide, air, methane, ethane, ethylene, propylene, propane, ethane/propane mix, butane, and pentane.

7. The inventory management method of claim 5, wherein the gas product is hydrogen.

8. The inventory management method of claim 5, wherein the impurities are selected from the group consisting of hydrogen sulfide, methane, carbon dioxide, nitrogen, ethane, and benzene.

9. The inventory management method of claim 5, wherein the gas product is hydrogen.

* * * * *